United States Patent
Venter et al.

(10) Patent No.: US 6,989,678 B2
(45) Date of Patent: *Jan. 24, 2006

(54) DETERMINING THE DIELECTRIC PROPERTIES OF WOOD

(76) Inventors: Liebrecht Venter, 15740 Palmer La., Haymarket, VA (US) 20169; Jacob Viljoen, 44 Alexander St., Stellenbosch (ZA), 7599

( * ) Notice: Subject to any disclaimer, the term of this patent is extended or adjusted under 35 U.S.C. 154(b) by 49 days.

This patent is subject to a terminal disclaimer.

(21) Appl. No.: 10/736,619

(22) Filed: Dec. 17, 2003

(65) Prior Publication Data

US 2004/0124856 A1 Jul. 1, 2004

Related U.S. Application Data

(60) Division of application No. 10/134,396, filed on Apr. 30, 2002, now Pat. No. 6,703,847, which is a continuation-in-part of application No. 08/913,429, filed as application No. PCT/US96/03604 on Mar. 14, 1996, now abandoned.

(30) Foreign Application Priority Data

Mar. 15, 1996 (ZA) .............................. 95/2126

(51) Int. Cl.
*G01R 27/26* (2006.01)

(52) U.S. Cl. .................. 324/663; 324/521; 324/683
(58) Field of Classification Search ................ 324/663, 324/661, 683, 521, 691, 709, 622, 76.52, 324/76.77; 73/304 C; 34/402
See application file for complete search history.

(56) References Cited

U.S. PATENT DOCUMENTS

| | | | |
|---|---|---|---|
| 3,252,086 A | | 5/1966 | Lundstrom |
| 3,430,357 A | | 3/1969 | Perry |
| 3,778,707 A | * | 12/1973 | Vogel .................... 324/659 |
| 3,805,156 A | * | 4/1974 | Norton et al. ............ 324/683 |
| 3,807,055 A | * | 4/1974 | Kraxberger ............... 34/402 |
| 4,107,599 A | | 8/1978 | Preikschat |
| 4,174,498 A | | 11/1979 | Preikschat |
| 4,259,632 A | | 3/1981 | Ahtiainen |
| 4,288,741 A | | 9/1981 | Dechene |
| 4,377,783 A | | 3/1983 | Wagner |
| 4,540,936 A | | 9/1985 | Walsh |
| 4,555,941 A | * | 12/1985 | Fathauer et al. .......... 73/304 C |
| 4,570,116 A | | 2/1986 | Tedd |
| 4,972,154 A | | 11/1990 | Bechtel |
| 5,070,725 A | | 12/1991 | Cox |
| 5,272,444 A | | 12/1993 | Cox |
| 5,654,643 A | * | 8/1997 | Bechtel et al. ............ 324/687 |
| 6,703,847 B2 | * | 3/2004 | Venter et al. ............ 324/663 |

OTHER PUBLICATIONS

Torgovnikov, G. I., Dielectric Properties of Woord, Springer Verlag, 1993, ISBN 3–540–55394, ISBN 0–387–55394, pp. 76–81.

James, W. L., Boone, R.S., Capacitive In–Kiln Wood Moisture Content Monitors, Wood Science, vol. 14, No. 4, Apr. 1982, pp. 146–154.

* cited by examiner

Primary Examiner—Anjan K. Deb
(74) Attorney, Agent, or Firm—Venable LLP; Andrew C. Aitken

(57) ABSTRACT

A wood drying installation for a wood drying kiln including a pair of electrodes adapted to be inserted into a wood stack contained in the kiln, a resistance connected in a series circuit with the electrodes, an AC voltage source connected to apply an AC voltage across the series circuit, a phase detecting circuit connected to the series circuit operable to generate a signal representing the phase angle between AC voltages applied to different parts of the series circuit, and a processor to receive the signal. The system is operable to determine a moisture value corresponding to a capacitive component of the reactive impedance between the electrodes in accordance with a predetermined arithmetic algorithm relating the value to the phase angle.

40 Claims, 7 Drawing Sheets

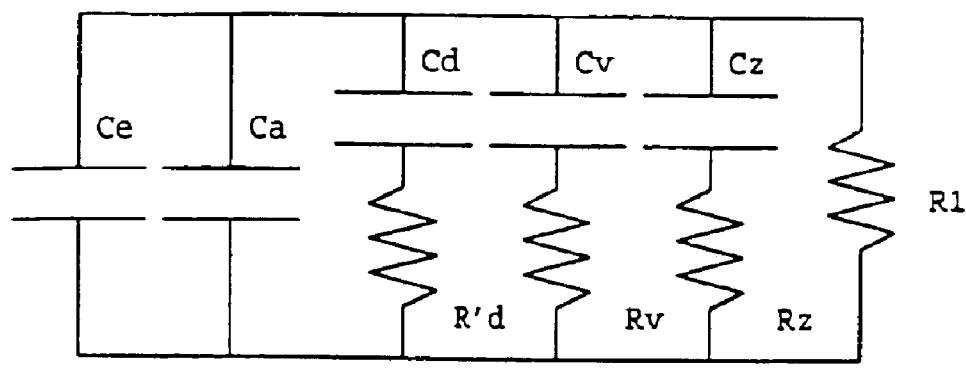
Figure 1: The equivalent circuit of Wood
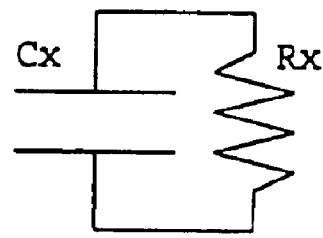
Figure 2: The general lumped model

DETERMINING THE DIELECTRIC PROPERTIES OF WOOD

CROSS REFERENCE TO RELATED APPLICATION

This application is a division of application Ser. No. 10/134,396 filed Apr. 30, 2002 now U.S. Pat. No. 6,703,847 which is a continuation in part of application Ser. No. 08/913,429 filed Dec. 11, 1997, which is a 371 of United States of America PCT/US96/03604 filed Mar. 14, 1996 now abandoned, both of which are hereby incorporated by reference.

This invention relates to a method of determining the dielectric properties of wood, in particular for purposes of deriving therefrom a measure of the moisture content of the wood, and to means for use in such method.

Definition of Terms

Moisture Content
  Defined as the following percentage, $$M.C. = 100 \frac{M_w M_d}{M_d},$$

where $M_w$ is the mass off wet sample and $M_d$ is the mass of the bone-dry sample.

Free water
  Water present in the trachea of the wood sample.
Bounded Water
  Water bounded to the cell walls of the wood sample.
Fiber Saturation Point (f.s.p.)
  The maximum moisture content where all water is absent from the trachea and all remaining water is bounded to the cell-walls.
  The typical f.s.p. for softwoods such as *Pinus* is 30%. For hardwoods, this is typically 30–40%. This however varies from species to species.

BACKGROUND OF THE INVENTION

When drying wood in a wood drying kiln, an end-point moisture content of 5% to 20% is normally required. Traditional methods of measuring the moisture content of wood, whilst reasonably accurate towards the end-point moisture content, become less accurate at higher values of the moisture content. At a moisture content of above 30%, the traditional methods become completely unreliable.

For the proper control of the environment in which wood is dried, for example, in a wood-drying kiln, it is important for the moisture content of the wood to be known accurately while the moisture content is still relatively high, e.g. above 30%. If the moisture content is accurately known at these relatively high values it becomes possible to accelerate the drying process considerably, without causing undue stresses in the wood.

The complexity of wood is easily under estimated. Wood is highly an-isotropic both in anatomy and by its electrical and dielectric properties. It is a complex composition of air, water cell-wall structure, organic materials such as cellulose, lignin and resins, inorganic salts and ion concentrations. The anatomy is comprised of solid cell-wall structures combined with trachea (tangential hollow tubes) which is either filled with water or air depending on the moisture content (m.c.) of the sample. Furthermore, variations within species is remarkably striking regarding ion-content which translates in conductivity and resistive variations. Species-to-species variations in ion content is even more influential and wide species to species changes in conductivity is experienced. In order to measure the dielectrics of such a complex medium, the influences of each of these components need be addressed before valuable and usable measurements and methods can be devised. The measurement of the dielectric properties of wood is particularly and unexpectedly troublesome as reported in detail in the book by Torgovnikov[C]. (The citations herein identified by upper case letters are o the bibliography at the end of the specification.) Not only is the dielectric highly an-isotropic and grain direction dependent, the unexpected temperature behavior of the conductivity of wood is worth mentioning. It would be expected that wood would have similar characteristics as usual carbon based resistors, which displays a decrease in conductivity with increased temperature (increase in resistance respectively). The conductivity of wood in fact does not follow this trend at all, but rather displays the temperature dependence strikingly similar to a semi-conductor i.e. the conductance increases with increasing temperature. It is clear that if this is not taken into account measuring methods of e.g. capacitance of the wood-dielectric will fail at elevated temperatures as large errors will be introduced. This particular fact resulted in several measurement systems to fail in industry for obvious reasons James[R]. To make matters even more troublesome, extremely non-linear anomalies occurs regarding the other relevant dielectric component namely the relative permittivity $\in_r$ also known in layman's terms as the dielectric constant. Since the relative permittivity gives rise to capacitance via the probe geometry and since capacitance will be what is measured, this influence will be discussed in terms of the capacitance but is equally valid for the relative permittivity. Dielectric constant and as a consequence capacitance increases substantially with increase in temperature compared to more homogeneous dielectrics. However, Torgovnikov [C] cites James's results to display the following anomalies. Not only is the relative permittivity and therefore capacitance wildly frequency dependent, it does so in an unexpected manner. Completely dry (bone-dry) wood has a relative permittivity of 4, while water has a relative permittivity of 80. The relative permittivity of water and bone-dry wood is for all purposes frequency independent except for the normal dispersion variations not of relevance here. However, when water and wood is combined i.e. wet wood is measured, we do not obtain the intuitive combined relative permittivity of 84, but instead values are reported by Torgovnikov and James [C] of $\in_r=650000$ at certain lower frequencies. This is most certainly an anomaly and to date still unexplained and seemingly not challenged however unlikely it seems. Furthermore the relative permittivity and therefore the capacitance increases dramatically with decrease in frequency compared to minimal change in $\in_r$ detected for pure water and bone-dry wood when not in combination over the same frequency range. In addition the loss-tangent tan δ, which is an indication of how lossy a material is in an applied electromagnetic field, also displays curious anomalies generally not expected from dielectric media. Even the most complex composites usually has a loss-tangent, for which each value of loss-tangent only one value of element of composition can be obtained. With wood as dielectric the loss-tangent generally becomes a relation i.e. the loss-tangent plotted against moisture content is that of a bell-curve Torgocvnikov [C] resulting in two moisture contents giving the same loss-tangent reading. This clearly cancels loss-tangent for measurement above f.s.p. in most cases as it results in ambiguity. These complications dwarfs the already significant an-isotropic behavior of $\in_r$ which has different values when the applied electromagnetic field is applied tangential and radially to the wood respectively. The remaining significant behavior of the wood-water relationship is at f.s.p, where free water starts to assemble in the hollow trachea and dissolves salts. These ions then drastically increase the conductivity above f.s.p. to enormous proportions and in effect making any correlation of moisture content above f.s.p. difficult if not impossible. The conductivity of wood therefore becomes an almost constant high value above f.s.p. literally independent of higher moisture contents. The reason for the sudden conductivity increase above f.s.p. is due to the minerals K, P, Al, Fe, Zn, Ca, Mn, Cl, Na and Mg, to name a few which are naturally encountered in wood. The majority of these minerals are dissolved and present in the free water as ions and therefore has a phenomenal influence on conductivity above f.s.p. Below f.s.p. no free water exists and these minerals are then deposited on the cell walls with less influence.

The bounded water (adsorbed water on cell walls) is also changed fundamentally in that the water which is now adsorbed by the cell-walls clearly cannot be rotated easily as a dipole in the applied field. As the wood dries the adsorption to the cell-walls increases giving even more resistance to rotation in the applied electromagnetic field. This results in a curved relationship between $\in_r$ at moisture contents below f.s.p. Above f.s.p. the free water in the hollow trachea are the dominant influence on $\in_r$ and $\in_r$ versus moisture content and the $H_2O$ molecules as dipole can easily and unrestrictedly be oriented in the applied electromagnetic field. This is the reason why $\in_r$ is then linear from f.s.p upwards to 200%. This combined then establishes a curve-linear relationship between $\in_r$ and the moisture content as empirically verified by Skaar[F]. It is therefore evident that two "types" of water exists in the wood-water combination and they influence the dielectric properties in a very different way. The list of behavioral anomalies are not exhausted as there are piezzo electrical effects creating electrical impulses during drying due to crystalline structures in the wood and several more which will not be discussed, although further complications arises due to them. Wood rivals if not champions the most complex composite dielectrics, is rich in anomalies and unexpected behavior. These anomalies and properties are crucial to understand why some measuring processes in prior art, when applied to wood, are irrelevant or non-functional and will be referred to in sequel.

Dielectric Model of Wood

It is well known from literature that the sensitivity of inductance to moisture content of wood is negligible. The dielectric for wood would then comprise of the various influences of dielectric constant $\in_r$ and conductivity $\sigma$ only.

The full dielectric model for wood is displayed in FIG. 1. All the different kinds of polarizations evident for wood are represented by the various capacitances. They are $C_e$ $C_a$ $C_d$ $C_v$ and $C_z$, effected by electronic, ionic, dipole, inter-facial, electrolytic, polarizations. $R_d$, $R_v$, $R_z$ and $R_f$ are the resistances resulting from energy losses at dipole, inter-facial, electrolytic, and resistance related to the direct current, respectively.

The model in FIG. 1 is for analytical purposes and a practical model used in determination of dielectric properties of wood for commercial systems is the Thevenin-Norton, lumped model as in FIG. 2 where the representative dielectric components are now the lumped values $C_x$ and $R_x$.

In the discussion below, it will be understood that the model as shown in FIG. 2 is used.

As a dielectric, wood is then comprised of physically and chemically inseparable components $R_x$ and $C_x$ combined in parallel to form an impedance. It is of utmost importance to understand that with wood as a dielectric, $R_x$ and $C_x$ cannot be treated as discreet components as one of the components cannot be physically removed from the medium to have only the other to remain and then just decide to measure one but ignore the other.

Correlation with Moisture Content

Several correlations of moisture content in wood are possible and are substantially researched, refereed, published and discussed by researchers in the field of wood-science.

Correlation of the Moisture Content with Conductivity

Conductivity manifests itself by means of resistance measurements and corresponds to conductivity according to the probe geometry used. As the bounded wood-water reaches a saturated state at around f.s.p. (30% m.c.), any moisture content above f.s.p. will result in free water condensing in the trachea. The salts deposited on the cell-walls then dissolves increasing the conductivity radically until a maximum is reached. The graph in FIG. 3 shows that it is not feasible to correlate conductivity with moisture contents above f.s.p. as there is not much resolution. This is the reason why resistive type measuring systems fails to give consistent readings above f.s.p. and can only measure in the shaded area correlation of the moisture content with the loss-tangent (tan $\delta$).

Correlation of Moisture Content with Loss-Tangent

Loss-tangent can be obtained from the conductivity and relative permittivity by means of $$\tan \delta = \frac{1}{\omega R_x C_x}.$$

It displays less of the restrictions of conductivity above f.s.p. but it is ambiguous as for every value of tan $\delta$ there exists two moisture contents. It is therefore usually only restricted to measurements below f.s.p. Since it is dependent on resistance, the values above f.s.p. will inherit the instabilities of resistance above f.s.p. due to hysteresis effects. FIG. 4 show how moisture content varies with loss tangent correlation of the moisture content with the dielectric constant Correlation of the Moisture Content with Dielectric Constant $\in_r$ This correlation manifests itself in capacitance measurements where capacitance is proportional to $\in_r$ by means of the probe geometry. Therefore all pure or exact capacitance measurements must correlate to moisture content according to the curve-linear graph such as in the FIG. 5.

As can be seen, there is no difficulty correlating pure capacitance with moisture contents above f.s.p. and the full range of moisture contents are available. These curves have been obtained and verified by Skaar, Uyemura, James at high frequencies and others under controlled conditions eliminating conductive influences. At lower frequencies capacitance has less influence on the impedance and conductance becomes dominant making it more difficult to obtain the same trend as the pure capacitance becomes obscured.

Definition of and Comparisons Between Resistive and Capacitive Sensors

It is of importance to focus on the two dielectric measurement principles namely "Capacitance" and "Conductivity" of the wood sample as is clear from the above descriptive of the dielectric model of wood. The classification of all the type of dielectric moisture measurement principles is now established.

It is clear that a measurement principle which claims to be a capacitance meter must be able to single out and measure only the capacitance $C_x$ in FIG. 1 and be generally insensitive to changes in $R_x$.

Likewise, a measurement principle which claims to be a resistance meter must be able to single out and measure only the resistance $R_x$ in FIG. 2 and be generally insensitive to changes in $C_x$.

Then, for a measurement principle to claim to be a loss-tangent meter $$\left(\tan \delta = \frac{1}{\omega R_x C_x}\right),$$

it must be clear that the meter combines the $R_x$ and $C_x$ components in such a way as to represent loss-tangent closely.

Any measurement principle unable to separate the components $R_x$ and $C_x$ in FIG. 1 will therefore be a non-linear convolution of dielectric properties and no fundamental information regarding $R_x$ and $C_x$ can be extracted. The output of such measurement is therefore some convoluted indication of the influences of both $R_x$ and $C_x$. This measurement type will be referred to as of "convoluted" type hereinafter.

Measurement methods which can measure and identify $R_x$, $C_x$ and tan $\delta$ accurately and independently will be described as "Pure-measurements" hereinafter.

Furthermore, if a single measurement principle can obtain all the separate dielectric properties at once and in real time, it will be called "real-time measurements" hereinafter.

It is important to distinguish between the type of cited measurement principles in the prior-art in order understand and appreciate the differences between the prior art when applied to wood as dielectric medium.

State of the Art

Ahtianien [N] discloses a method by which he claims to measure capacitance of an organic material as dielectric e.g. grain. The circuit proposed there, measures only the amplitude of the alternating voltage over a capacitance C, and then rectifies it by an ideal solid state rectifier. The circuit is analyzed as follows.

The oscillator generates a real valued alternating voltage $V_o$ and the voltage across the dielectric to be measured is defined as $V_d$. Since the input impedance of the operational amplifier is extremely large very little loading or error will be introduced on the dielectric containing C. The circuit will therefore show $$|V_d| = \left|\frac{Z_d}{Z_d + R_1} V_d\right|$$

as the output of this circuit. It is clear from the body and specification of the patent that the author defines his model for the dielectric of wheat as that of a capacitance C only. In order to apply and evaluate the method of Ahtianien to wood as a dielectric, we need to replace the Capacitance C representing the dielectric with that of a capacitance in parallel with a resistance to represent wood as shown in FIG. 2. We then analyze the performance of this invention on the model for wood. Since wood as a dielectric is comprised of two physically inseparable components namely $R_x$ and $C_x$, and since Ahtianien assumes that there are no or negligible influences of $R_d$ present, we will now refer to the situations where $R_d$ is varied. We use published data on the properties of wood to construct an example. From Torgovnikov[C], we obtain tables for dielectric properties of wood at elevated temperatures. Consider the case of density $$\rho = 0.5 \left[\frac{g}{cm^3}\right],$$

temperature T=90° C. and moisture content m.c.=40%. The dielectric properties listed at these conditions are tan $\delta$=24 and $\in_d$=221. Assuming the most basic probe setup namely, a parallel plate probe with the mentioned wood-dielectric disposed between it and choosing the area of the plates as ratio to distance between them $$\frac{A}{d} = 1,$$

we obtain the capacitance as $C_d = \in_0 \in_r = 1.956$ nF, where $$\varepsilon_0 = 8.8510^{-12} \left[\frac{F}{m}\right]$$

is the permittivity constant of the free vacuum. A trivial calculation using $$\tan \delta = \frac{1}{\omega R_d C_d} \text{yields,}$$

yields, $R_d$=339 $\Omega$ for wood using the published data.

The percentage error introduced by not considering the resistance in the dielectric for the invention as in [N] is now investigated. Since the dielectric of wood is comprised of a capacitance in parallel with a resistance, we now conclude by considering two cases. The first calculating the output voltage of the circuit as intended by Ahtianien, meaning without the resistance connected in parallel with the capacitor as in his circuit and then repeating the calculation when a resistor is connected in parallel with a capacitor of the same value as the first test. Ahtianien discloses that he chooses $R_1$ for every suitable measuring range by means of choosing it equal to the reactance of the capacitive component. Since we calculated the capacitance from the published data, the value for $R_1$ as required by Ahtianien equates to 8.136 k$\Omega$. By comparing the values obtained at the output of his invention by means of the percentage $$\frac{VZ_C - VZ_{R//C}}{VZ_C},$$

where $VZ_C$ is the output voltage when an impedance with a capacitance only is connected to the circuit as dielectric, while $VZ_{R//C}$ is the output voltage from the circuit with the dielectric comprising of the same capacitance connected in parallel with a resistance. The values of capacitance and resistance as calculated for wood under the conditions of the published data will now be used. After trivial calculation the results show an error in excess of 90% obtained when the method of Ahtianien is used on wood as dielectric i.e. measuring wood but ignoring the influence of resistance $R_d$. The invention of Ahtianien can therefore only measure a dielectric for which the resistive component is negligible and is therefore not applicable to the measurement of wood as a dielectric as was clearly shown. It is therefore of the convoluted type as defined and described above in the section under subtitle "Definition of and Comparisons between Resistive and Capacitive Sensors." Clearly Ahtianien's method fails when used with wood as a dielectric. Athanien would typical show a capacitance almost double the value of the actual value of the capacitance contained in wood as dielectric medium which is clearly unacceptable.

Vogel [J] discloses a method by means of measuring the loss-tangent tan δ to determine moisture content. It would not be unacceptable to assume that the method presented by Vogel measures loss-tangent (tan δ) accurately and that we may discuss his method in terms of tan δ as he do claim in the title and claims of his patent. The reader is referred to consult the exact same data used for Ahtianien from the table found in Torgovnikov[C]. Upon inspection of the loss-tangent at $$\rho = 0.5 \left[ \frac{g}{cm^3} \right],$$

T=90° C. it is clear that tan δ has a maximum at about 30%. As stated above, it is not acceptable to have a single measurement correlated with two possible moisture contents as outcomes as ambiguity clearly results. Based on the cited public data, if the instrument of Vogel indicates tan δ=29, then two moisture contents will be displayed by the instrument, namely 20% m.c. and 100% m.c. An operator not informed about the present state of the wood will have no way of knowing which of the two moisture contents are the correct one. It is clear that this method and all other methods based on tan δ can only be used when the wood is either known to be very wet or very dry in advance. To make matters worse, the maximum in tan δ shifts with temperature and frequency further limiting it's use and further necessitating even more hindsight. Upon closer inspection of FIG. 5 in vogel, it is seen that indeed, Vogel constrained his measuring apparatus severely by only allowing measurements between 8–15% m.c. out of the normal 0–200% m.c. required for a full range measurement method. It must be noted in addition that the principle of Vogel is dependent on reference components in the form of an accurate 90° phase-shift and that he uses this phase shift to obtain the complex current of the dielectric resembling the loss-tangent. It must also be evident that since Vogel only measures the complex current, insufficient data prevents separation of the exact values of $C_x$ and $R_x$, as loss-tangent is dependent on both of these dielectric components. This application can therefore be classified as obtaining an approximated form of the loss-tangent by measuring a property closely related but not exactly the loss-tangent tan δ.

Lundström [B] does not disclose that sinusoids are used or measured across the dielectric to be measured or phase angle is sensed. A resonance technique is used in the form of a tank circuit as the measurement principle. It also discloses that a current is measured which is then used to approximate the power loss. The power loss is related to a measurement which can isolate $R_x$ out of the complex dielectric which also includes $C_x$. The description of the patent does disclose that the circuit attempts to obtain $R_x$ independently from $C_x$. The method however is not capable of obtaining $C_x$ and is in effect still dependent thereof as is strikingly evident in the manner compensations are used to eliminate the effects of $C_x$. The method used in this application clearly uses a method of "brute force" to attempt to get rid of $C_x$. The method relies on the connection of a large capacitance in parallel with the tank circuit containing the wood dielectric. It is disclosed that this larger capacitance is then used to obscure the capacitance in the dielectric in order to eliminate it's effects. It can be deduced with certainty that this method cannot obtain $C_x$ at all. The method also discloses that the application of the device is by means of comparison i.e. a reference sample of known moisture content is first measured, then other samples are compared in reading with the reading of this reference sample. There is therefore no exact relationship to moisture content for this measurement principle, nor is there any claim their measurement is related to published moisture vs dielectric property relationships. It must be noted in passing that the "large capacitor" as used is selected of magnitude μμf. This is usually equal to pF (pico Farad). Almost all wood containing moisture content displays capacitance far in excess of 10 pF so the units and the text are contradictory in description. The author probably meant 10 mF=10 000 μF, as this would be used to force the imaginary part $$\frac{1}{j\omega C_x}$$

of the impedance to zero (if the frequency is chosen to be relatively low) although it is hardly an acceptable method to suppress the influences of $C_x$ compared to a method which would calculate the influence of $C_x$ and subtract the known influence. It is disclosed that $R_x$ is measured or correlated with moisture but as explained above such a method cannot measure above f.s.p. The description also discloses that the measurement system is dependent on power supply variations and temperature influences and that hardware implementations need be introduced. In this regard thermisters are introduced to temperature compensate the design against thermal drifts.

Ted [A] discloses a method by which he measures resistance or reactance of which the latter can be constructed from either a capacitance or inductance. It is not disclosed in the patent that combinations of say $R_x$ and $C_x$ can be measured simultaneously. In fact the description indicates that there are three different methods by which each of $R_x$, $C_x$ and $L_x$ are obtained. This is then classified as a composite method unable to obtain $R_x$ and $C_x$ accurately when combined into a single dielectric to be measured. Ted also discloses hardware compensations necessary to eliminate power supply variations and oscillator amplitude variations. To conclude, the opening sentence in the claims states that the invention measures selectively, either $R_x$ or $C_x$ or $L_x$ but not combinations thereof.

Kraxberger [M] does not disclose that his circuit measures E, but he claims he measures the impedance. If we assume that he does incorporate E to obtain an impedance measurement another question arises. It must be remembered that the impedance of a wood dielecteric is complex i.e.

$$Z_x = R_x + \frac{1}{j\omega C_x}.$$

Therefore in order to obtain the complex impedance, the phase angle between I and E must also be known. None of these items are described and it becomes clear that the method is meant to measure only the magnitude of the complex impedance. It is also clear that no phase detection of any sort is performed. The method can therefore not be used to obtain to pick out $C_x$ and $R_x$ from a parallel combination and obtain them accurately. It must be noted that the amplitude of the complex impedance of the wood dielectric is dependent on $R_x$ and therefore will have detrimental influence on measurement above f.s.p as explained in above. It is also disclosed that the system can only work satisfactory if the probing cables are shielded and where the shield is driven in anti-phase to the applied signal for the purpose of eliminating the probe-cabling capacitances. This is therefore a hardware implementation to illuminate probe-cable capacitances. It is also important to note, that this application uses a single plate as a probe. It is also noteworthy that this probe is equipped with standoffs as displayed in FIG. 4. The reason for this is to eliminate the influence of conductivity and therefore $R_x$ in order to present some form of resistive isolation and reduce currents from flowing with contact. This is in fact the attempt to eliminate the influence of $R_x$ in the complex impedance of the wood dielectric. Isolation of probes proved unsuccessful and was investigated by James and Boone [R] who tested similar systems in great detail with mixed results. The equivalent circuit in FIG. 2 displays a bridge circuit by which only $C_4$ can be adjusted to bring the bridge into balance. It is well known that in order to obtain both $R_x$ and $C_x$ from the complex dielectric, at least two components in a bridge needs to be varied. The circuit in FIG. 2 therefore establishes that the method cannot pick out $Z_x$ and $R_x$ from a parallel combination and obtain them accurately.

Perry [O] discloses a method by which a bridge is connected to the wood complex dielectric. Perry acknowledges that the wood displays two properties namely $R_x$ and $C_x$. He then correctly discloses in his description that as wood dries, $C_x$ decreases while $R_x$ increases. Perry then correlates exactly this dynamic with moisture content. Perry uses one conductive plate as probe to the dielectric. The invention of Perry is basically similar to Kraxberger[M]. Both uses a capacitive bridge connected to the dielectric by means of a conductive plate and the imbalance of the bridge is then correlated to the moisture content.

Bechtel [G] discloses an invention for small sample online measurement of grain-direction and not moisture content. No relevance is found.

Preikschat [H] discloses that the relative permittivity increases with increase in conductivity. As this statement is true for some instances it might not necessary be true for all condition of wood. If it is remembered that $$\omega R_x C_x = \frac{1}{\tan \delta},$$

and that /tan/delta generally resembles a bell-curve w.r.t. moisture content from 0–100% James in Torgovnikov[C], and since it is known that the relative permitivity $\in_r$ is curvilinear and monotonic but tan δ not necessarily so, establishes $R_x$ as not necessarily monotonic which is in stark contrast with this statement. Should you have a method by which you can measure $R_x$ and $C_x$ accurately, there would be no need to compensate $C_x$ for changes in $R_x$. Since Preikshat has to compensate $C_x$ w.r.t changes in $R_x$, his method and the compensation is contained in one of the claims, he therefore most probably do not obtain $R_x$ and $C_x$ accurately from the complex dielectric and a resulting influence of $R_x$ on $C_x$ is encountered.

Walsh [K] discloses a method by which he first detects the resonant frequency of a tank circuit of which the dielectric, comprising of $R_x$ and $C_x$ is measured in soil samples. The variable components "120" and "122" are then used to obtain the frequency of resonance. He then utilizes the equations $$W^2 = \frac{1}{R_1 R_2 C_1 C_2} \text{ and } \frac{V_2}{V_1} = \frac{1}{1 + \frac{C_2}{C_1} + \frac{R_1}{R_2}}$$

at this specific resonant frequency. The problem with this method is, that $R_x$ and $C_x$ when wood is the chosen dielectric, is extremely frequency dependent as was mentioned above and by James[P]. For the case of wood containing 100% m.c. at a temperature of 90° C., $\in_r$=600000 at 20 Hz and 27 at 1 MHz. In general any organic dielectric will have different moisture contents as it absorbs or loses moisture as time passes. This will demand from Walsh's method to select a different resonant frequency at every different time of measurement. This is not the case for soil and ceramics in general and $R_x$ and $C_x$ remains frequency independent with varying moisture content. For wood therefore Walsh's method would clearly require additional information and families of curves for each set of resonant frequency and moisture content which could have been avoided by a method fixed at a single chosen frequency. This method therefore fails to measure the severely frequency dependent dielectric of wood as the two equations presented by Walsh are not sufficient. The method of Walsh should then need to be used at 3 frequencies, with an extra equation in order to eliminate frequency. It is therefore not adequate to measure the dielectric of wood and fails the objective as described as a predefined frequency cannot be chosen and one is left to have to accept whatever the resonant frequency is Walsh's method selects. If a user demands $R_x$ and $C_x$ of wood at a specific frequency, Walsh's method fails as described in the text as an extra equation is needed.

Wagner [L] discloses a method for measuring the moisture content of Veneer. The application is not relevant, the method involves measuring the amplitude of the current through a detector which is then correlated to moisture content. No phase detection or voltages measured claimed or described and no separation of the components of the complex wood dielectric is evident or claimed.

Dechene [Q] discloses a method for measuring the current flowing through the capacitance of a liquid dielectric. The method was devised with objective to measure a very small capacitance in the presence of a very large conductance of a liquid. The purpose of the invention therefore is to correlate with capacitance $C_x$ of the medium and not $R_x$. The operation is as follows, since the capacitive current component will be 90° shifted with the conductance current, the method revolves around introducing a phase shift of 90% to create two signals differing by this phase shift. These two signals are then used in a summation to cancel out the conductive current from the complex current obtained from the dielectric sample. This invention proposes to achieve by means of a hardware implementation to obtain and single out the current through $C_x$ only from the complex dielectric. This invention therefore measures a quantity proportional to $$i_c = C_c \frac{\partial V_x}{\partial \partial t},$$

where $V_x$ is the voltage across the $C_x$.

Cox [S] and [T] disclose a method by which the voltage across a dielectric, the current through the dielectric and the phase difference between these two signals are obtained. In FIG. 5 of Cox[T], the impedance is clearly stated as meaning impedance as ohms, thereby explaining that impedance is to mean the magnitude $|Z_x|$ of the complex impedance $Z_x=|Z_x|e^{j\theta}$ and not the complex impedance itself. Percentage water is clearly correlated there with the magnitude of impedance, which results in a measurement correlation with m.c. equal to that of Kraxberger although the methods differ largely. The fundamental difference is that the phase angle is explicitly used to detect water-cut, but not for calculating the complex impedance $Z_x$. The complex impedance is therefore not obtained in this application.

To conclude, James & Boone 1982[R], in the conclusion of that publication, clearly stipulated the need that technologists and inventors should move away from measuring only the magnitude of the impedance in early 1980 and concentrate on obtaining the components of the complex dielectric. James in a report circa 1997[U], expressed the same sympathies establishing that pure capacitance was still not implemented commercially due to technical difficulties.

OBJECTIVES OF THE INVENTION

A first objective of the invention is to implement a system which can obtain the true values of both $R_x$ and $C_x$ independently in order that if both are known, either is obtained at it's true value. It can be concisely stated as obtaining a method by which $$\frac{\partial C_x}{\partial R_x} \equiv 0 \text{ and } \frac{\partial R_x}{\partial C_x} \equiv 0.$$

This is described in more detail to follow.

As stated above, $R_x$ and $C_x$ are physically inseparable and chemically bound into the wood dielectric. Any method which claims to measure e.g. only $C_x$ without disclosing how $R_x$ was removed effectively to obtain the correct or pure value of $C_x$ free of any influence of $R_x$ up to the limits of measurement resolution is questionable. Failure to do so, will result in measurements called e.g. capacitance or capacitive, but which will still be dependent on variations of $R_x$ and vice versa. This is then surely not measuring the true or pure value of capacitance and or the true value of resistance $R_x$. As the values of $C_x$ and $R_x$ are givens it is up to the method to separate and compensate efficiently to obtain the pure values of these two properties. The state of the art will now tested against this objective.

Ahtianien [N] clearly ignores the resistive component of the complex dielectric. By means of an example based on public measured data presented by the most renowned researchers, it was shown that the method of Ahtianien introduces errors of almost the same magnitude as the value for capacitance measured. It therefore clearly fails when applied to wood as dielectric.

Vogel discloses to measure tan δ and does so by means of only measuring the complex current through the dielectric. He discloses this current resembles the loss-tangent. Measuring only the complex current through the dielectric, does indeed give a relationship which resembles the loss-tangent, but it is not the exact loss-tangent $$\tan \delta = \frac{1}{R_x C_x}.$$

It is clear that one cannot just say the loss-tangent is the current through the dielectric or e.g. the inverse current. The method is therefore not exact and of the correlated type and fails the objective set out above as the method as described cannot obtain $R_x$, $C_x$ individually according to the objective and thereby construct $$\tan \delta = \frac{1}{R_x C_x}$$

accurately and only correlates to tan δ.

The method of Lundström [B] gets rid of $C_x$ influences by brute force. The impedance of the complex wood dielectric is $$Z_x = R_x - j\frac{1}{\omega C_x}.$$

By placing another extremely large capacitance in the order of 10 mF (10 milli Farad) across the impedance in $Z_x$ (effectively in parallel with $C_x$), it is clear from the equation of $Z_x$ that the reactive part will be reduced to zero if the frequency remains low. This will indeed give the result as Lundström [B] anticipated. It does fulfill the objective partly for $R_x$ but fails as it cannot obtain $C_x$.

Ted [A] discloses a method which can only measure discreetly and he does not claim that he can measure $R_x$ and $C_x$ when in combination. He only discloses a method by which he can measure either one or another property. Ted thereby fails the above-mentioned objective as the wood dielectric is physically indivisible and cannot be treated as discrete components i.e. just a resistor or just a capacitor as dielectric measuring either $C_x$ or $R_x$.

Preikschat [I] discloses a method by which only the current through the dielectric sample is measured. The measurement principle is identical to Vogel[J], but the method of implementation differs. Furthermore no phase of this current is detected making it inferior to the measurement of Vogel as it only measures the amplitude of the current which is then normalized to be related to the amplitude of the impedance. It clearly fails the objective set as it clearly cannot separate $R_x$ and $C_x$ form the complex dielectric.

Perry discloses not to measure or attempt to separate the values of $R_x$ and $C_x$ out of the complex dielectric. He discloses to measure the combined effect of how $R_x$ and $C_x$ changes and correlates the combined change with moisture content. In principle this again involves measuring the amplitude of the current through the impedance $Z_x$ and is almost identical in principal to Vogel [J] and Preikschat [I] but differs slightly in application.

Preikschat [H] discloses a method where he do claim to obtain outputs corresponding to $1/R_x$ and $j\omega C_x$. However, he also discloses that his voltage output relating to $j\omega C_x$ is dependent on $R_x$ which fails the test of the objective as his method cannot obtain the independent values accurately in order that $$\frac{\partial C_x}{\partial R_x} \equiv 0 \text{ and } \frac{\partial R_x}{\partial C_x} \equiv 0.$$

Walsh [K] do have a method based on resonance, which is demonstrated to have the credibility and ability to separate out $R_x$ and $C_x$.

Wagner [L] discloses a method for measuring the current flowing through the dielectric. This have been treated under Vogel [J] and Preikschat [I] and fails the objective for the same reason as the principle is basically identical but the application different.

Dechene [Q] measures the current through the capacitance $C_x$ of the dielectric medium. His measurement is therefore correlated with $$C_x \frac{\partial V_c}{\partial t}.$$

Cox [S] and [T] discloses a method by which the magnitude $|Z_x|$ of the complex impedance and the phase difference between current and voltage through and over the dielectric is measured. No attempt or disclosure was made obtaining $R_x$ and $C_x$ from the measurements and it was not correlated to water and or oil mixtures. The magnitude of the impedance can be obtained by the equation $$|Z_x| = \left|\frac{V}{I}\right|$$

which clearly does not involve a phase measurement to obtain and therefore no need to calculate the complex impedance. To conclude, no separation of dielectric components was disclosed attempted or achieved. It therefore fails the first objective.

A second objective is obtaining true valves of $R_x$ and $C_x$ independently, simultaneously and instantaneously. This means that with a single measurement at a specific moment of time all the necessary information must be able to be gathered by the method to obtain $R_x$ and $C_x$. The reason for this specification is that wood as a dielectric may undergo reasonably fast changes in moisture contents, therefore simultaneous measurements are crucial to minimize errors due to changes occurring due to e.g. loss of moisture content. Preikschat [H] can in principle be used to measure simultaneously, but it fails the objective of independent measurement of $R_x$ and $C_x$. Dechene [Q] can only measure in real time if the drying rate of the dielectric is much slower than the time constant of the long term integrators disclosed in his method. Long term integrators, 4 and 30 could introduce aliasing if the time constant is in the order of the drying rate. The objective is therefore not met in general. Ahtianien[N], Vogel[J], Lundström, Ted[A], Kraxberger [M], Preikschat[I], Perry[O], Walsh [K] can measure $R_x$ and $C_x$ simultaneously and it is not unreasonable to assume that his circuit would be able to find the resonant frequency in a very short time. It therefore achieving the second objective as specified.

A third objective is to measure $R_x$ and $C_x$ as in the second objective while being restricted to a specified frequency. Most of the cited patents can be adjusted to measure at a predefined frequency. However, Ahtianien[N], Vogel[J], Lundström [B], Ted[A], Preikschat[I], Perry Preikschat[H], Wagner[L], Dechene[Q], Cox [S] and [T] all failed to conform to the first and second objectives and therefore fail the third objective as a consequence.

Walsh [K] conforms to the first and second objectives as mentioned, but fails the third objective in an interesting but catastrophic way when applied to wood as will now be explained. For wood $C_x$ and $R_x$ are extremely frequency dependent, while in contrast it is not the case for soil, as the dielectric is not severely frequency dependent. Walsh's method will select a different resonant frequency at every different moisture content. The method therefore cannot present the moisture content at a predefined frequency, as the resonance frequency cannot be chosen but is seeked by the method to obtain resonance corresponding to the product $R_x C_x$. In more detail, Walsh's method cannot eliminate the frequency dependence of the wood dielectric as he has now three variables $R_x$, $C_x$ and $\omega$ with wood as dielectric but only two equations disclosed. It therefore fails the objective. It is questioned whether Walsh's method could be brought into resonance for all moisture, temperature and density conditions when wood is used as dielectric due to the extremely large frequency and other dependencies evident due to problems with low Q-factor. Low Q-factor will cause the resonance circuit to "hunt" and not be able to find the resonance due to a very flat peak of the Q-factor maximum.

A fourth objective is to measure $R_x$ and $C_x$ as in the second objective whereby in addition moisture content above f.s.p. can be measured.

To measure above f.s.p. is one of the longest outstanding problems in moisture measurement of wood. State of the art only achieved measuring slightly above f.s.p. The need for industry to have moisture content measurement above f.s.p. is immense. By having such an instrument, large loads of expensive lumber can be dried with moisture driven schedules and errors in drying rates and distributions can be fixed in real time from 200% m.c. downward. The state of the art implemented in drying kilns can only do so from 30% downward and gives no indication above 30% leaving the operator in the blind during the first 60% of the drying schedule. This has been explained in detail above where it was shown that any measurement principle or method depending on conductivity or equivalently $R_x$, will inherit the problems above f.s.p. as is encountered with $R_x$. It is also stressed again that merely using two parallel plates does not constitute a capacitive measurement as conductivity is also measured with such a "capacitance" setup. As there is a lot of ambiguity in the use of the term "capacitive" and "capacitance" in literature, meaning anything from a parallel plate geometry to measuring the actual capacitance of a dielectric, the applications will be listed with comments although all the cited patents fail as none could conform to the third objective. The state of the art regarding f.s.p. is as follows. Ahtianien [N] ignores the influence of $R_x$ and is therefore dependent on conductivity. Any conductivity dependence results in inability to measure above f.s.p as described in [REF:Introduction] fails the objective. Using a capacitive probe will obviously not guarantee measuring pure capacitance as the invention cannot remove the detrimental influence of $R_x$ above f.s.p. Vogel [J] discloses to measure tan δ only. As explained above tan δ is not injective and has a maximum between 0–100% m.c. Thereby failing the objective as ambiguity arises. Lundström [B] only measures $R_x$ so it cannot be used reliably above f.s.p. as described above and fails the objective. Ted [A] fails to obtain $C_x$ independent of $R_x$ and will therefore be dominantly conductive above f.s.p. and fails the objective. Kraxberger [M] measures the magnitude of the impedance of the complex, dielectric and therefore is dependent on $R_x$. It therefore cannot measure reliably above f.s.p. and fails the objective. Perry [O] fails the objective same reason as Kraxberger does. Preikschat [I] fails for the objective same reason as Kraxberger does. Walsh [K] can measure $C_x$ independent from $R_x$ but he cannot do so successively at the same frequency. Extra equations are needed in his disclosure to effect this. These equations were not disclosed mentioned or anticipated in his disclosure and it therefore fails to measure $C_x$ and $R_x$ above f.s.p. as both are extremely frequency dependent. Wagner [L] cannot remove $R_x$ from the measurement. It therefore cannot measure reliably above f.s.p. and fails the objective. Dechene [Q] can remove the current flowing through $R_x$ from the complex current through the dielectric. The quantity $$i_c - C_c \frac{\partial V_x}{\partial \partial t}$$

might be able to be used for measurement above f.s.p. However, Ahtianien[N], Vogel[J], Lundström [B], Ted[A], Preikschat[I], Walsh[K], Perry, Preikschat[H], Wagner[L], Dechene[Q], Cox [S] and [T] all failed to conform to the third objectives and therefore fail this objective by default.

A fifth objective is to proud a system whereby f.s.p. can be detected observing when $R_x$ desaturates. If $R_x$ can be obtained independently from influences of $C_x$, then a reliable method can be obtained to establish f.s.p. as can be immediately understood from the above section headed by the subtitle "Correlation of the Moisture Content with Conductivity". Fiber saturation point can be defined to be triggered when the conductivity starts to drop sharply from it's saturated state and or when the slope of the curve reaches 45°. To explain the effect; As soon as all the free water is removed out of the trachea and the only remaining water are bounded water, the conductivity will tend to decrease sharply. This will have the effect that $R_x$ will increase sharply. This is then an accurate method to obtain the f.s.p. Obtaining f.s.p. is of crucial importance for the European kiln drying community as they need f.s.p. detection to speed up their drying after it is detected. It is general knowledge that once f.s.p. has been reached the drying rate can be increased as the damage to the wood would now be minimal compared to fast drying rates above f.s.p. This has immense impact on the cost, as shorter drying times can be achieved with the same quality produced. In summary of the problem, if $R_x$ is not known independently from the influences of $C_x$, fiber saturation point cannot be obtained. Mere magnitude of impedance measurements will therefore be dependent on $C_x$ and fail to allow use of $R_x$ to detect f.s.p. The state of the art relates as follows, Ahtianien [N] ignores the influence of $R_x$ and therefore it is not calculated or detected and become known. It fails the objective. Vogel [J] discloses measuring tan δ only so there is a dependence on $C_x$. It fails the objective. Kraxberger [M] measures the magnitude of impedance and is therefore dependent on $C_x$. It fails the objective. Perry [O] fails for the same reason as Kraxberger and fails the objective. Cox [S] and [T] fails for the same reason as Kraxberger and fails the objective. Preikschat [I] cannot obtain the independent values of $R_x$ and $C_x$ accurately. It therefore fails the objective. Wagner [L] fails for the same reason as Kraxberger and fails the objective. Dechene [Q] discloses to measure $C_x$ by removing $R_x$. $C_x$ cannot be used to detect f.s.p. as no known phenomena is known to detect f.s.p. It therefore fails the objective. Lundström [B] would be able to detect fiber saturation point as he eliminates $C_x$. Walsh [K] would be able to measure f.s.p. as it can measure $R_x$. Since f.s.p. is frequency independent it passes the objective.

A sixth objective is to provide a system whereby moisture content can be correlated by using published analytical correlations based on $\in_r$, σ.

The dielectric properties of wood namely $\in_r$ the relative permittivity and the conductance σ, generates all other properties such as tan δ, $C_x$, $R_x$. Correlation of $\in_r$ and σ to moisture content of wood is published by researchers working in all fields spanning modeling to empirical measurement. In order to correlate using the data from researchers in public domain, measuring principles must disclose to measure $\in_r$ and σ within the limits of resolution of the measuring hardware and software. This is of utmost importance. If a measurement principle is used for a medium and there are already published data correlating the moisture content with a dielectric property rigorously, then it is of utmost importance to obtain a measurement method which measures the dielectric properties individually and accurately and independently in order that this public data can be used to correlate the moisture content. The problem with methods not conforming to this philosophy is that custom correlations with moisture needs to be made which become relevant only to the method and since it might be a linear superposition of dielectric properties cannot be verified and tested against public data. The benefit on the other hand of a method accurately measuring the dielectric properties is that all other custom correlations can be emulated by a method measuring the dielectric properties accurately. The converse is not true. An instrument based on a method which measures a lumped super-position of dielectric properties cannot produce one of these dielectric properties accurately. The benefit is clear. The cited inventions will now be tested toward if they can be correlated to one of these properties. This is of extreme importance since it discloses whether the wealth of public domain data can be used with the method.

Ahtianien [N] does not correlate purely to $C_x$ or $R_x$, and therefore cannot correlate with σ or $\in_r$ of the dielectric as described above. Vogel [J] discloses to measure a quantity resembling tan δ and can arguably correspond to the public data, but there is no proof presented whereby he measures the actual or pure $$\tan \delta = \frac{1}{\omega R_x C_x}$$

by means of equations in the disclosure. Lundström [B] does disclose a method by which he eliminates the influence of $C_x$ in his measurement. Although no equation is presented to prove that $R_x$ is in fact measured, the benefit of the doubt that he can correlate his output to that of $R_x$, is plausible due to his compensation for $C_x$. It might therefore be possible to accurately correlate with $R_x$ and the objective might possibly be reached. Kraxberger [M] measures the magnitude of the complex dielectric and therefore does not relate to any of the properties above but to inseparable combinations thereof. It therefore fails the objective. Perry [O] fails the objective for the same reason as Kraxberger[M]. Preikschat [I] discloses that his separation of the reactive and conductive components are not ideal as $C_x$ is influenced by changes in $R_x$. The resulting correlations with $j\omega C_x$ and $R_x$ are disclosed to be combined into a single measurement correlated to moisture content. It therefore fails the objective for at least $C_x$. Walsh [K] can be used with the published correlations, as he can measure $R_x$ and $C_x$ accurately for at least some frequency ranges. The problem is however that he have to relate each and every frequency possible that his method chooses. It however does correlate to data at a non-specified frequency so it satisfies the objective, but it would fail immediately if correlation at a specified frequency is chosen as the criteria. Wagner [L] fails the objective for the same reason as Kraxberger. Cox [S] and [T] fails the objective for the same reason as Kraxberger. Dechene [Q] might be possible to correlate with $C_x$ by transforming his current correlation to a capacitance correlation and is allowed to satisfy the objective.

A seventh objective is to provide a system by which the probe dielectrics can be removed and have insignificant influence on the measurement.

In this regard, the method must be such that if any stray or offset values are generated by the probe dielectric, that it can be systematic removed by the method of the invention in order to obtain only the value of the dielectric under measurement without the probe offsets. Ahtianien [N] does not disclose a probing system. However if a probing system involves a resistive offset, then it would not be able to compensate in any case and therefore fails the objective.

Vogel [J] discloses to measure $$\tan \delta = \frac{1}{\omega R_x C_x}$$

and is not able to measure $C_x$ and $R_x$ independently. There is no way therefore to know what $R_x$ and $C_x$ are by only knowing the loss-tangent and therefore the probe dielectrics cannot be calculated and therefore not compensated for. It therefore fails the objective. Ted[A], cannot measure the properties of a dielectric with combined element $R_x$ and $C_x$ and therefore cannot in general calculate and remove the probe influence on the measurements.

Lundström [B] measures only $R_x$ assuming he can obtain $R_x$ accurately, then he can remove the probe resistance $R_0$ by measuring the short circuited resistance of the probe and conforms to the objective. Kraxberger[M], Perry[O], Wagner[L], Dechene [Q] and Cox [S] and [T] measures the magnitude of the complex impedance either by current voltage ratios or by current alone assuming the voltage across the dielectric is constant. The magnitude of the complex impedance can be compensated for if $R_x$ and $C_x$ is known which is not the case. They therefore fail the objective.

Preikschat [I] would be able to measure the offsets of some probes except when these probe-sets are lossy by which his application clearly states that $C_x$ becomes dependent on $R_x$. It therefore fails the objective in general.

Walsh [K] would be able to eliminate the probe dielectrics if the probe dielectrics are frequency independent. As the latter is true in almost all cases it can be viewed as practically true and satisfies the objective.

An eighth objective is to provide a system which is intrinsically free of power and oscillator amplitude variations and references needed.

The objective here is to set the standard for a method which is independent of oscillator variations in a fundamental sense. Meaning that the compensation is integral and do not need to be added by means of discreet components whose existence is due only to this compensation. If such methods exist, they will clearly be superior in ruggedness and long term stability compared with hardware implications thereof. The use of references are costly as it means components with discreet accuracy. Any method free of dependence on references are clearly superior to those in need of it. Ahtianien [N] relies on his oscillator voltage to be an accurate reference. Fluctuations in oscillator specifications are not compensated for. Oscillator voltage will otherwise influence his measurement voltage and therefore fails the objective. Vogel [J] needs a reference phase shift of exactly 90° for his method to operate and therefore fails the objective. Inaccurate phase shift will result in inaccurate measurement.

Lundström [B] needs a reference capacitance of enormous magnitude in order for his circuit to work as described. He also discloses in his objectives that he needs to compensate for power supply variations and fails the objective. Kraxberger [M] needs 180° out of phase reference voltages to eliminate the influence on $C_x$ by the cabling. If Kraxberger [M] satisfied the seventh objective, the cumbersome out of phase probe construction would have been unnecessary since $C_x$ could be measured and subtracted. It fails the objective. Perry [O] does not compensate for oscillator variations and therefore fails the objective as his measurement will be dependent on amplitude variations.

Preikschat [I] relies on a reference phase shift for his invention to operate as described. In the description, it is disclosed that a stabilized oscillator is required. It therefore fails the objective on both accounts. Walsh [K] would be independent of oscillator voltage in a fundamental sense and need no compensation as all oscillator amplitude variations are dissipated in the ratio $$\frac{V_2}{V_1}.$$

Wagner [L] does not compensate for oscillator variations and the measured quantity will therefore be dependent on oscillator variations. It fails the objective. Dechene [Q] does not compensate for oscillator variations. The readings will therefore be dependent on oscillator variations and it fails the objective. Cox [S] and [T] satisfies the objective for the same reasons as in Walsh[K].

A ninth objective is to provide a system in which the probes need not be cleaned or isolated from the dielectric regarding measurement of $C_x$. Contact resistance between wood and metallic probes are extremely significant. When the objective is to measure pure capacitance $C_x$, and the method used does not compensate for removing conductivity or equivalently $R_x$, then it will be needed to isolate the metallic probes from making contact with the medium to try and compensate in part for such error influences on the true capacitance. It must be stressed again that $C_x$ and $R_x$ cannot be physically and electrically isolated. Therefore a method with the objective to measure pure capacitance capacitive, should not dependent on contact between the wood and the metal probes. This will involve effective canceling of the conductance effects of the dielectric. Only processes displaying the ability to calculate both $R_x$ and $C_x$ or which does not calculate $R_x$, but clearly shows that the $C_x$ measurements are compensated for by means of eliminating the $R_x$ influence will qualify to be considered for this objective. James and Boone [R] describes this in detail and presents case studies involving state of the art "capacitive" kiln monitors failing this criterion. These "capacitive" monitors in fact measures the magnitude of impedance but are called capacitive due to the fact that the probing systems resembles capacitive geometries and not by the quantity it measures.

All prior art which did not satisfy the criteria of the first objective are disqualified. They are; Ahtianien[N], Perry[O], Wagner [L] Preikschat[I], Cox [S] and [T]. Lundström [B] will most likely not have to isolate the probing system and satisfies the objective. Dechene [Q] would not need to isolate the probes and complies with the objective. Walsh [K] would not need such isolation, but as usual will fail to obtain $C_x$ at a specified frequency. It however satisfies this objective.

Dechene [Q] would not need to isolate the probes and complies with the objective.

This concludes the objectives.

SUMMARY OF THE INVENTION

In the system of the invention all of the above described objectives are met. The method is based on the principle of measuring only three properties namely the voltage over the impedance comprising of the complex dielectric of wood as described above, a voltage over a resistance in series with the impedance and the phase shift between these two voltages. The physically and chemically inseparable dielectric properties $C_x$, $R_x$ are then obtained uniquely independently and mutually exclusive of another by the use of a mathematical model. The loss-tangent tan δ can be constructed by either using the values $C_x$ and $R_x$ obtained or from an expression involving only the three measurements utilizing the mathematical model.

According to the present invention there is provided a method of determining the dielectric properties of wood, which method includes having the wood disposed between electrodes, applying a varying electrical signal to the electrodes, measuring the electrical values of the signal, and determining from the measured values the phase angle and magnitude of the complex impedence between the electrodes.

The varying electrical signal can conveniently be a sinusoidal voltage and can be applied to the electrodes via a resistive element, and the phase angle between the applied voltage (i.e. the voltage before the resistive element) and the voltage across the electrodes (i.e. the voltage after the resistive element), and the magnitudes of said voltages determined. From this it is possible to derive the phase angle and magnitude of the complex impedance between the electrodes.

It will be understood that one of the electrodes may be ground, i.e. the structure on which the wood is supported, where the structure is of an electrically conductive material.

The measured values may be determined in an electronics module which is in close proximity to the electrodes, and the phase angle and magnitude of said complex impedance may be determined from the measured values in data processing means which is remote from the electrodes, there being a data link between the electronics module and the data processing means.

Further according to the invention there is provided means for determining the dielectric properties of wood, which comprises a pair of electrodes between which the wood can be disposed, and means for determining the phase angle and magnitude of the complex impedance between the electrodes.

Still further according to the invention there is provided a wood-drying installation which comprises a wood-drying kiln and means for determining the moisture content of wood being dried in the kiln, said means comprising a pair of electrodes between which the wood in the kiln can be disposed, and means for determining the phase angle and magnitude of the complex impedance between the electrodes.

The means for determining the phase angle and magnitude of the complex impedance between the electrodes may comprise a resistive element connected in series with one of the electrodes, means for applying a sinusoidal voltage to the electrodes via the resistive element, and means for determining the phase angle between the applied voltage and the voltage across the electrodes and the magnitudes of said voltages.

The invention will now be described in more detail, by way of example, with reference to the accompanying diagrammatic drawings.

BRIEF DESCRIPTION OF THE DRAWINGS

FIG. 1 is a circuit diagram of an equivalent circuit for the full dielectric model of wood;

FIG. 2 is a circuit diagram of a simplified equivalent circuit assumed in the system of the invention;

DETAILED DESCRIPTION OF THE INVENTION

Figure 6:
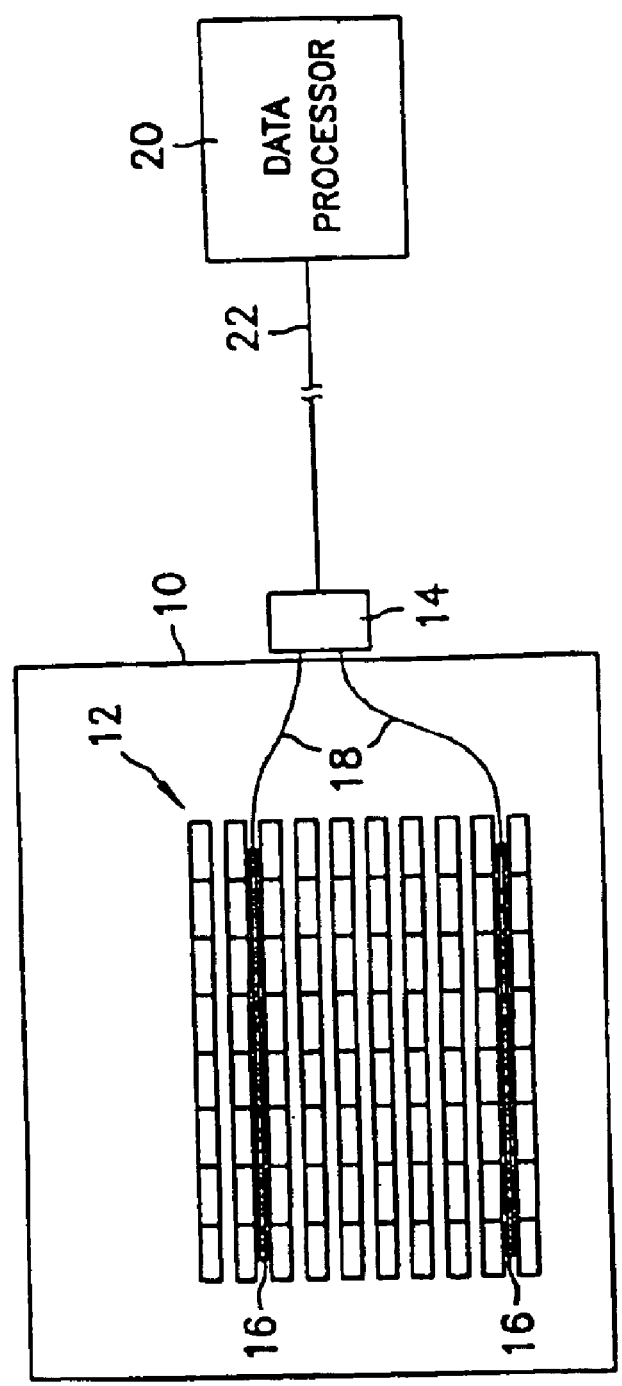
FIG. 6 is an end view of a stack of timber, in a wood drying kiln provided with measuring means in accordance with the invention.

Referring to FIG. 6 in more detail, reference numeral 10 indicates a wood-drying kiln in which there is a stack of timber 12. The timber 12 is arranged in layers which are spaced from one another by means of spacers. The environment inside the kiln is controlled according to the moisture content of the timber.

To determine the moisture content of the timber accurately, the kiln is provided with measuring means comprising an electronics module 14 outside but in close proximity to the kiln, a pair of electrodes 16 inside the kiln and coupled to the module 14 by means of electrical connections 18, and a remote data processor 20 which is connected to the electronics module 14 by means of a data link 22. Where there are a number of kilns 10, each with its own electronics module 14, the various electronics modules may all be connected to the same data processor 20.

The electrodes 16 are in the form of metal plates and are simply inserted into the spaces between layers in the stack 12. It is an important feature of the invention that the electrodes 16 need not be cleaned prior to insertion into the stack, as operation of the apparatus is not affected by the degree of physical contact with the timber. The size and exact position of the electrodes is also not important. If the size and/or position of the electrodes is changed, all that will be required is for the system to be recalibrated.

Figure 7:
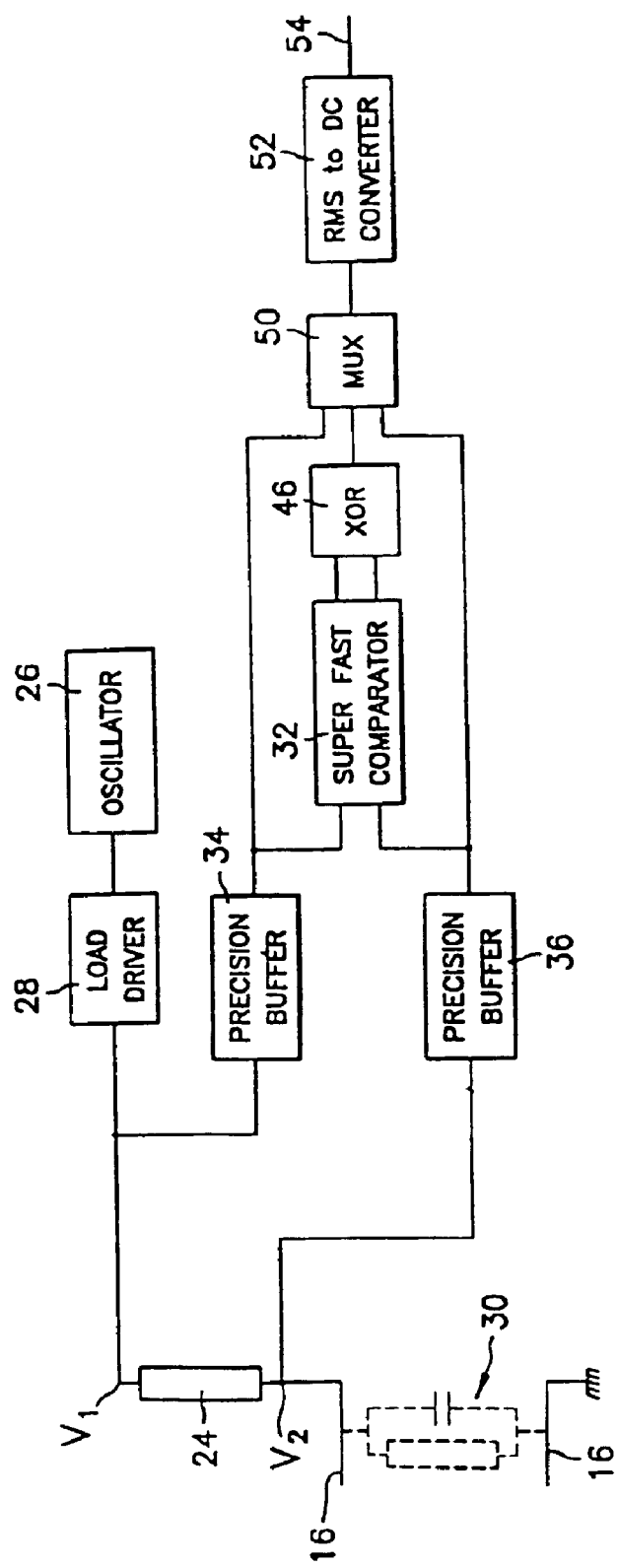
FIG. 7 is a block diagram of the measuring means.

The electronics module 14 serves to measure the values that are required to determine the capacitance and resistance of the complex impedance between the electrodes 16. This is achieved in the following manner. The electronics module, as shown in FIG. 7, includes a resistive element 24, connected in series with one of the electrodes, and an oscillator 26 and associated driver 28 whereby a sinusoidal voltage can be applied to the electrodes via the resistive element. The oscillator 26 has a frequency which is in the ultra-sonic range, for example in the order of 40 kHz. The impedance indicated at 30 represents the impedance between the electrodes 16.

The electronics module 14 further comprises a super-fast comparator 32 which is connected via a precision buffer 34 to the output of the driver 28, and via a precision buffer 36 to one of the electrodes, the other electrodes being connected to ground.

Figure 4:
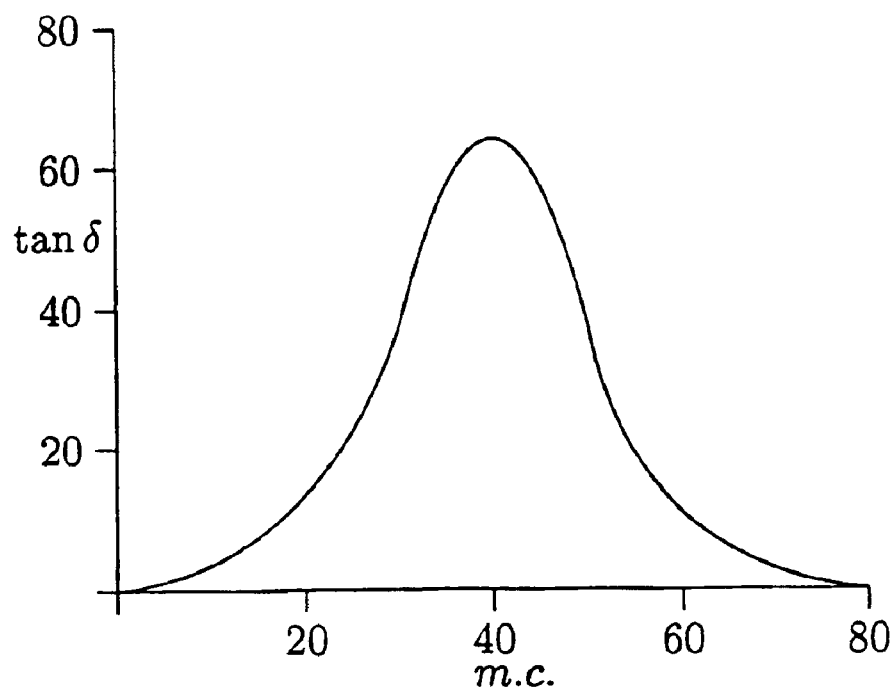
FIG. 4 is a curve showing the variation of the loss tangent with the moisture content of wood.
Figure 8:
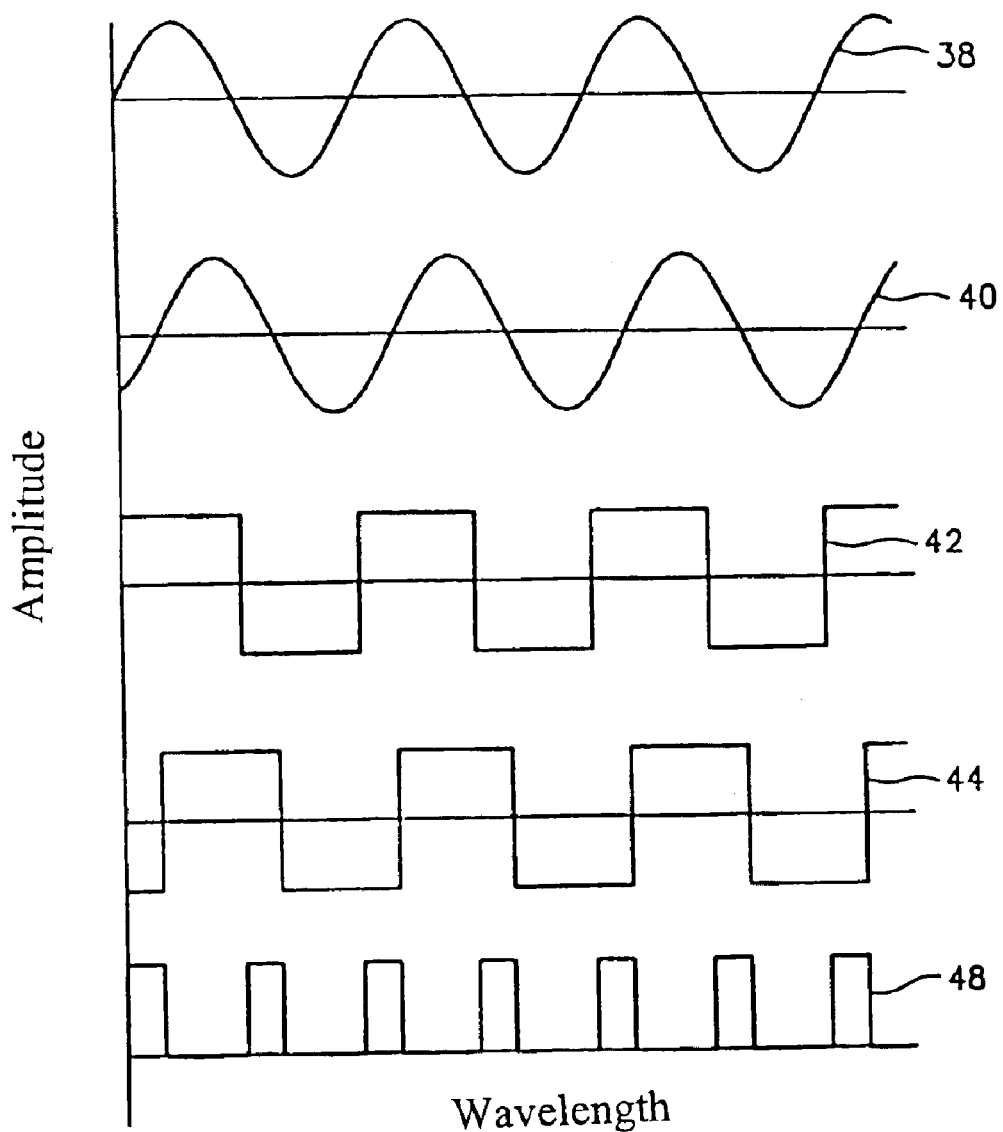
FIG. 8 shows certain voltage waveforms.
Figure 9:
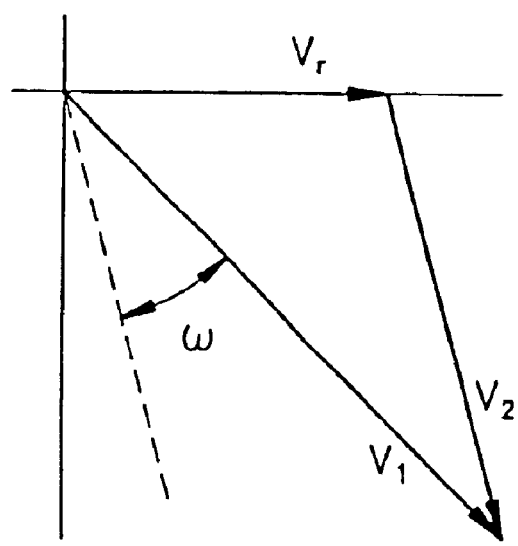
FIG. 9 is a phasor diagram of the voltages.

The waveform of the applied voltage (i.e. the output of the driver 28) is indicated at 38 in FIG. 8, whereas the waveform of the voltage across the electrodes 16 (i.e. after the resistive element 24) is indicated by reference numeral 40 in FIG. 8. In FIG. 9 the applied voltage 38 is indicated by the phasor $V_1$ and the voltage across the electrodes by the phasor $V_2$. Because the impedance 30 is a complex impedance, there is a phase difference between the voltages $V_1$ and $V_2$, this being indicated by the angle φ in FIG. 4. $V_x$ in FIG. 4 is the voltage across the resistive element 24.

The comparator 32 serves to convert the sinusoidal voltage 38 and 40 to square-wave voltages 42 and 44 respectively.

Figure 3:
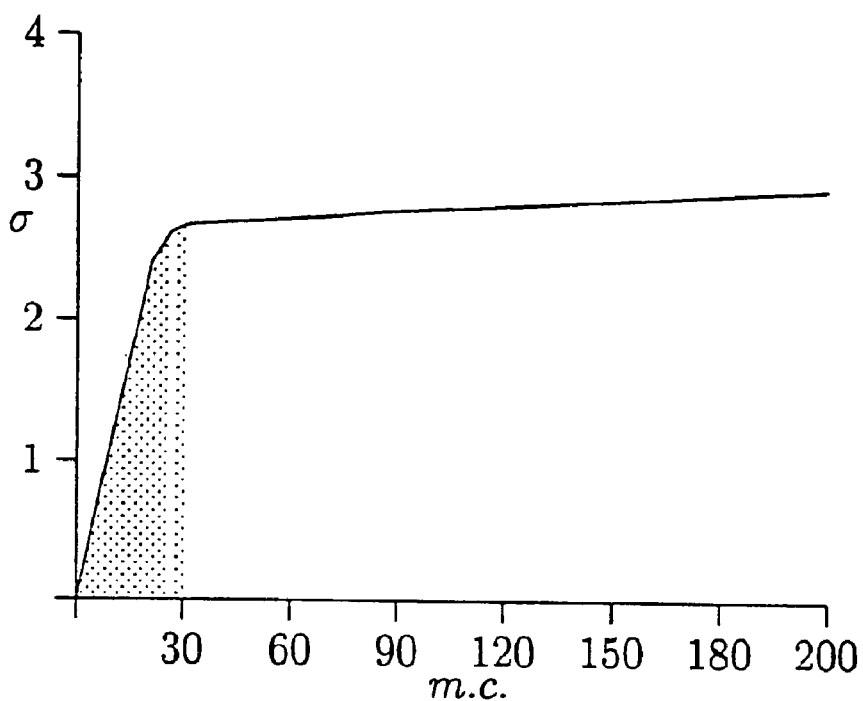
FIG. 3 is a curve showing the variation of the conductivity of wood with the moisture content of wood.

The electronics module 14 further comprises an exclusive OR (XOR) circuit 46 whose output is indicated at 48 in FIG. 3. The RMS value of the output 48 varies in proportion to the phase difference between the voltages 38 and 40. The outputs of the buffers 34 and 36 and the output of the XOR circuit 46 are fed via a multiplexer 50 to an RMS-to-DC converter 52. The multiplexer 50 has a relatively slow sampling rate as compared with the frequency of the applied signal.

Output 54 of the RMS-to-DC converter 52 is relayed to the data processor 20 via the data link 22.

The phase angle of the impedance 30 is determined by making use of the following equations:

$$a = V_2 * \cos\phi$$

$$b = V_2 * \sin\phi$$

$$d = V_1/\{-a*a/b - 1\}$$

$$c = a*d/b$$

$$C_x = d/R_s * 2\pi f$$

$$R_x = R_s(-c-1)$$

Where: $V_1$ is the amplitude of the applied voltage;
$V_2$ is the amplitude of the voltage across the electrodes;
φ is the phase difference between the voltage $V_1$ and $V_2$;
$R_s$ is the series resistive element 24;
f is the frequency of the applied voltage;
$C_x$ is the value of the capacitive component of the complex impedance 30; and
$R_x$ is the resistive component of the complex impedance 30.
assuming that the capacitive and resistive components of the impedance are in parallel as shown in FIG. 2.

In the event that the complex impedance includes an inductive component ($L_x$) in parallel with the capacitive component $C_x$, the value of $L_x$ can be determined independently from $C_x$ by measuring the complex impedance at two different frequencies.

The capacitive and resistive components of the complex dielectric as depicted in FIG. 7 is obtained rigorously by means of the following procedure. Element 30 in FIG. 7 is represented as $Z_x$, meaning the parallel combination of the resistive $R_x$ and capacitive $C_x$ properties of the wood sample.

The load impedance $Z_x$ (30) is connected in series with the resistor $R_s$ (24) and the voltage $V_2$ is measured across the load. The principle measurement is then the comparison between the applied voltage $\overline{V}_1$ connected to the remaining side of $R_s$ and the load voltage $\overline{V}_2$ which also involves a phase detection.

Expressing the impedance in terms of the dielectric elements $C_x$ and $R_x$ and the angular frequency ω, the impedance of the dielectric medium can be obtained in terms of $R_x$ and $C_x$ as $$Z_x = \frac{R_x Z_c}{Z_c + R_x} \quad (1)$$

Expanding this equation by first substituting with $$Z_c = \frac{1}{j\omega C_x}$$

then expanding into real and imaginary parts, the impedance becomes $$Z_x = \frac{R_x}{1 + \omega^2 C_x^2 R_x^2} - j\frac{R_x^2 C_x \omega}{1 + \omega^2 C_x^2 R_x^2} \quad (2)$$

Rewriting this in terms of magnitude and angular components using the Euler description yields, $$\|Z_x\|e^{j\theta} \quad (3)$$

where $\|Z_x\| = \frac{R_x}{(1 + \omega^2 C_x^2 R_x^2)}\sqrt{1 + R_x^2 C_x^2 \omega^2}$ and $\theta = \arctan(-\omega R_x C_x)$.

It is a trivial exercise to obtain, $$Z_x = \frac{R_s \overline{V}_2}{\overline{V}_1 - \overline{V}_2} \quad (4)$$

Since $\overline{V}_1$ is the oscillator voltage, the phase angle of this sinusoid is zero. The waveform obtained at $V_2$ will display some amplitude decrease due to e.g. the dielectric loss of the medium (wood) and also display a phase difference φ due to the 80|1 polarization ratio of the $H_2O$ molecules and the cell-wall structure in the presence of the electromagnetic field.

Therefore define, $\overline{V}_1 = V_1$ and $\overline{V}_2 = V_2 e^{j\Phi}$. By substitution for $\overline{V}_1$ and $\overline{V}_2$ in equation (4) into and after expanding into $\overline{V}_1$ and $\overline{V}_2$ real and complex parts and finally rewriting in Euler form, the following is obtained.

$$Z_x = \frac{R_s V_2 e^{j(\phi+\delta)}}{\sqrt{V_1^2 + V_2^2 - 2V_1 V_2 \cos\phi}} \quad (5)$$

where $$\delta = \arctan\frac{V_2 \sin\phi}{V_1 - V_2 \cos\phi} \quad (6)$$

Similarly this is written in Euler form as $$Z_x = \|Z_x\|e^{j(\phi+\delta)} \quad (7)$$

Since the impedances of equation (7) and (3) and are the same in magnitude and phase angle it follows that, θ=φ+ δ2kπ and $$\frac{R_s V_2}{\sqrt{V_1^2 + V_2^2 2V_1 V_2 \cos\phi}} = \frac{R_x}{(1 + \omega^2 C_x^2 R_x^2)}\sqrt{1 + R_x^2 C_x^2 \omega^2}$$

Ignoring multiple solutions, assuming k=0 and substituting for θ and δ in the phase equation, and obtain, $$\arctan(-R_xC_x\omega) = \phi + \arctan\frac{V_2\sin\phi}{V_1 - V_2\cos\phi} \quad (8)$$

By taking tan on both sides of the equation and using the identity, $$\tan(A+B) = \frac{\tan A + \tan b}{1 - \tan A \tan B} \quad (9)$$

it follows after some simplification that $$-\omega R_x C_x = \frac{\sin\phi V_1}{V_1\cos\phi - V_2} \quad (10)$$

which is the reciprocal of the loss tangent. The equation (10) substituted into equation (2) is sufficient to obtain $R_x$ uniquely in terms of the amplitudes $V_1$, $V_2$ and their relative phase shift $\phi$. After some extended simplifications it is found that $$R_x = \frac{R_s V_2}{V_1\cos\phi - V_2} \quad (11)$$

$C_x$ is obtained in turn by substituting equation 11 into equation 10. After some trivial simplifications the capacitance $C_x$ is obtained as, $$C_x = \frac{V_1\sin\phi}{V_2 2\pi f R_s} \quad (12)$$

These values are mathematically the same as:

$R_x = R_s/(-c-1)$ and $C_x = d/R_s{}^*2\pi f)$ where $a = V_2\cos\phi$, $b = V_2\sin\phi$, $c = a{}^*d/b$, and $d = V_1/\{-a{}^*a/b - 1\}$ Take note that capacitive phase angles are negative, therefore $\phi$ would be negative resulting in the capacitance $C_x$ to be positive.

The following achievements are obtained.

It is clear from the above derivation and equations and that by only measuring the magnitudes $V_1$, $V_2$ and the phase angle $\phi$ between these two sinusoids, that the capacitance $C_x$ and the resistance $R_x$ can be obtained exactly within the resolution of the measurement of $V_1$, $V_2$ and the $\phi$. It must be stressed that $C_x$ is obtained independently $R_x$ and that variations of one do not influence the other due to inaccuracies introduced by the method and vice versa. The only dependence that can be introduced is due to the minute errors created during measuring of these three quantities. A method is therefore established whereby the pure values of $R_x$ and $C_x$ are obtained independently, instantaneously and simultaneously once $V_1$, $V_2$ and $\phi$ are known. It can also operate at a specified frequency within its frequency range.

The mathematical model obtains exact values of $R_x$ and $C_x$ not depending on any hardware except $R_s$ and of measurement principles to obtain $V_1$ and $V_2$ accurately. It is clear from the equations 11 and 12 obtained that $R_s$ can be dynamically altered to suit for measurements without loss of accuracy as it is contained in the equations. There is therefore a minimal dependence on hardware reference restricted to only that of $R_s$ and the accurate measurement of two voltages $V_1$ and $V_2$. The remainder is done by exact formulas to obtain $R_x$ and $C_x$.

Furthermore the loss-tangent can be constructed from $C_x$ and $R_x$ by the equation $$\tan\delta = \frac{1}{\omega R_x C_x}$$

or instantly from the same measurement of $V_1$, $V_2$ and the phase angle $\phi$ using the equation $$\tan\delta = \frac{V_2 - V_1\cos\phi}{V_1\sin\phi}$$

The model also takes care of oscillator variations in a fundamental way. The equations are such, that any variations of oscillator amplitude due to power fluctuations etc are compensated for elegantly and intrinsically without the need for any hardware implementation. The magnitudes $V_1$ and $V_2$ are related as follows.

$$\frac{V_2}{V_1} = \left\|\frac{Z}{R_s + Z}\right\| \quad (13)$$

From this it is clear to see that $C_x$ and $R_x$ in equations 11 and 12 will be invariant under any variations of $V_1$ and as a consequence also tan $\delta$ as it is constructed uniquely from $C_x$ and $R_x$.

Figure 5:
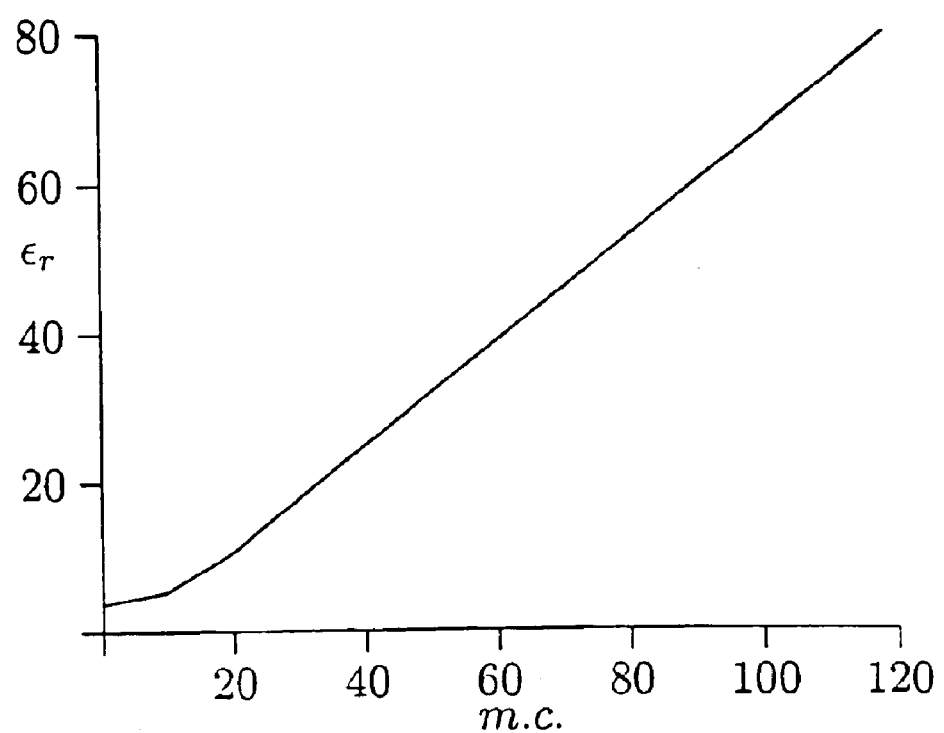
FIG. 5 is a curve showing the variation of the capacitance in the complex impedance of wood with the moisture content of wood.

Since the measurement principle can detect $R_x$ and $C_x$ independently, the resistance and capacitance of the probe wiring can be elegantly removed. Since Capacitances add in parallel, the probe wire capacitance can simply be subtracted from the capacitance measured with a load attached in order to obtain the capacitance of the wood sample as $C_L = C_T - C_C$, where $C_L$, $C_T$ and $C_C$ are the load, total and cable capacitances respectively. The parallel resistance of lossy probe systems is also accurately measured and can be trivially removed by means of $$\frac{1}{R_L} = \frac{1}{R_T} - \frac{1}{R_p},$$

where $R_T$ is the total resistance measured, $R_L$ is the load resistance and $R_p$ is the probe parallel resistance. The instantaneous measurement of capacitance and resistance by the method therefore easily systematically and clearly removes the cable dielectric properties in order to obtain the dielectric properties of the medium independent from cable dielectric influences. From the valve of $C_x$ the moisture context of the wood can not be determined as indicated by FIG. 5.

Since the pure value of $C_x$ can be measured by this method, measurement of moister content above f.s.p. is immediately evident as the influence of $R_x$, which obscures this measurement, is removed. Similarly, since the pure value of $R_x$ can be obtained, the exact value of f.s.p. can be correlated as the influences of $C_x$, which obscures detection of f.s.p. on $R_x$ is eliminated.

The method elegantly removes the probe dielectric influences on the measurements as the probe dielectrics can be measured and the capacitance subtracted from the capacitance obtained with a dielectric connected and probe resistance obtained removed from the resistance obtained with a dielectric connected by means of the formula for two resistances in parallel.

Furthermore, since $C_x$ and $R_x$ are obtained in their pure form by this method and since the probing system is just a proportionality between the $C_x$ and $\in_r$ and $R_x$ and $\sigma$ it can be related directly with public data.

The application of a measuring system to constitute a meter to perform the tasks as described in this method is described in detail in the parent application Ser. No. 08/913,429 and will be understood to apply to this continuation in part thereof. The following notational difference is introduced. In this continuation in part $\omega$ shall mean the angular frequency $\omega=2\pi f$, where f is the frequency. In the parent application $\omega$ was understood to mean the phase difference between the sinusoids related to $V_1$ and $V_2$ which is rather indicated as $\phi$ in this continuation. The series resistor R in the parent application is renamed to $R_s$. By substitution of the equations a, b, d and b as found in the parent application, $C_x$ and $R_x$ obtained yields exactly the equations as derived in this continuation application.

The above described system measures the capacitance and resistive of a reactive load represented by a stack of wood produced between two probes. In accordance with the invention, the reactive load is connected in a series circuit with a known resistance and the voltage across the reactive load and across the series current are detected. The phase angle between the two voltages is determined and from the values of the known resistance, the voltages, and phase angle between the detected voltages, the capacitance and resistance are determined in accordance with arithmetic equations expressing the capacitance and resistance in terms of the measured values. It will be appreciated that instead of detecting the voltage across the series circuit, the voltage across the known resistance could be detected, and the phase angle between this voltage and the voltage across the reactive load measured. From these voltages, the value of the known resistance, and the phase angle, the capacitance and the resistance of the reactive load could be determined from arithmetic equations in a similar manner.

BIBLIOGRAPHY

[A] Ted et al, U.S. Pat. No. 4,570,116, Feb. 11, 1986.
[B] Lundrostrõm, U.S. Pat. No. 3,252,086, Jul. 16, 1962.
[C] Torgovnikov, G. I. Dielectric Properties of Wood, Springer Verlag, 1993, ISBN 3-540-55394, ISBN 0-387-55394.
[D] Spiegel M. R. Advanced Mathematics, McGraw Hill 1971.
[E] Venter, L. R. Viljoen, JPS Method of Determining the Dielectric Properties of Wood, and Means for use in such Method.
[F] Skaar C., 1948, The dielectric properties of wood at several radio frequencies. NY State Coll for, Syracuse, N.Y., Tech Publ 69.
[G] Bechtel F. K. et al., Nov. 20, 1990. U.S. Pat. No. 4,972,154.
[H] Preikschat F. K., Apparatus and method for providing . . . U.S. Pat. No. 4,174,498, Nov. 13, 1997.
[I] Preikschat F. K., Electrode for an Impedance measuring . . . U.S. Pat. No. 4,107,599, Aug. 15, 1978.
[J] Vogel R. F., Means for measuring Loss-Tangent . . . U.S. Pat. No. 3,778,707, Dec. 11, 1973.
[K] Walsh J. E., Soil Moisture Sensor . . . U.S. Pat. No. 4,540,936, Sep. 10, 1985.
[L] Wagner D. W., Moisture Detector. U.S. Pat. No. 4,377,783, Mar. 22, 1983.
[M] Kraxberger G. S., Method and Apparatus for measuring the moisture content of wood. U.S. Pat. No. 3,807,055, Apr. 30, 1974.
[N] Ahtianien A. J., Continuous action capacitive moisture measurement apparatus. U.S. Pat. No. 4,259,632, Mar. 31, 1981.
[O] Perry W. D., Method of drying wood and Moisture Indicator. U.S. Pat. No. 3,430,357, Mar. 4, 1969.
[P] James W. L., Dielectric Properties of Wood and Hardboard, 1975 US Forestry Research Paper FPL-245.
[Q] Dechene et al., Electrical measurement of fluid . . . U.S. Pat. No. 4,288,741, Sep. 8, 1981.
[R] James W. L., Boone, R. S., Capacitive In-Kiln Wood Moisture content Monitors, Wood Science Vol. 14 No. 4, April 1982.
[S] Cox P. T., Dielectric cross-plot water cut monitoring apparatus and method, U.S. Pat. No. 5,272,444, Dec. 21, 1993.
[T] Cox P. T., Water-Cut monitoring means and method, U.S. Pat. No. 5,070,725, Dec. 21, 1993.
[U] James W. L. Electric Moisture Meters for Wood. United States Department of Agriculture, Forests Products Laboratory, Report FPL-GTR-6.

What is claimed is:

1. A wood drying installation comprising a wood drying kiln, electrodes adapted to be inserted into wood contained in said kiln, a resistance connected in a series circuit with said electrodes, an AC voltage source connected to apply an AC voltage across said series circuit, a phase detecting circuit connected to said series circuit operable to generate a signal representing the phase angle between AC voltages applied to different parts of said series circuit, and a processor connected to receive said signal and operable to determine a value corresponding to a capacitive component of the reactive impedance between said electrodes in accordance with a predetermined arithmetic algorithm relating said value to said phase angle.

2. A wood drying installation as recited in claim 1, wherein the voltages applied to different parts of said series circuit comprise a voltage applied across said electrodes and the voltage applied across said series circuit.

3. A wood drying installation as recited in claim 1, wherein said arithmetic algorithm expresses said value as a function of said phase angle, said voltage, and said resistance.

4. A wood drying installation as recited in claim 1, wherein said processor determines the capacitance of said reactive impedance.

5. A wood drying installation as recited in claim 1, wherein said phase detecting circuit converts said AC voltages applied to different parts of said series circuit to square wave voltages and an exclusive OR circuit receiving said square wave voltages.

6. A wood drying installation as recited in claim 5, wherein said circuit further comprises an RMS-to-DC converter connected to receive the output of said exclusive OR circuit.

7. A method of measuring the moisture content of a stack of wood in a kiln comprising placing electrodes in said stack of wood in said kiln, connecting a known series resistance in series with said electrodes, applying a AC voltage across said series circuit, detecting AC voltages applied to different parts of said series circuit, determining the phase angle between said AC voltages applied to different parts of said circuit, and calculating a value corresponding to the capacitive reactance of the reactive impedance between said electrodes in accordance with an arithmetic algorithm relating said phase angle, V1 and V2 to said capacitance value.

8. A method as recited in claim 7, wherein said value comprises the capacitance of said reactive impedance.

9. A method as recited in claim 7, wherein said voltages applied to parts of said series circuit comprise the voltage applied across said series circuit and a voltage applied across said electrodes.

10. A method as recited in claim 7, wherein said arithmetic algorithm expresses said value as a function of said phase angle, said voltages, and said resistance.

11. A system for measuring reactive impedance of a material adapted to be inserted in said material, comprising a resistance connected in a series circuit with electrodes, an AC voltage source connected to apply an AC voltage across said series circuit, a phase detecting circuit connected to said series circuit operable to generate a signal representing the phase angle between AC voltages applied to different parts of said series circuit, and a processor connected to receive said signal and operable to determine a value corresponding to a capacitive component of the reactive impedance between said electrodes in accordance with a predetermined arithmetic algorithm relating said value to said phase angle.

12. A system as recited in claim 11, wherein the voltages applied to different parts of said series circuit comprise a voltage applied across said electrodes and the voltage applied across said series circuit.

13. A system as recited in claim 11, wherein said arithmetic algorithm expresses said value as a function of said phase angle, said voltages, and said resistance.

14. A system recited in claim 11, wherein said processor determines the capacitance of said reactive impedance.

15. A system as recited in claim 11, wherein said phase detecting circuit converts said AC voltages applied to different parts of said series circuit to square wave voltages and an exclusive OR circuit receiving said square wave voltages.

16. A system as recited in claim 15, wherein said circuit further comprises an RMS-to-DC converter connected to receive the output of said exclusive OR circuit.

17. A method of measuring the reactive impedance of a material comprising placing electrodes in said material, connecting a known series resistance in series with said electrodes, applying a AC voltage across said series circuit, detecting AC voltages applied to different parts of said series circuit, determining the phase angle between said AC voltages applied to different parts of said circuit, and calculating a value corresponding to the capacitive reactance of the reactive impedance between said electrodes in accordance with an arithmetic algorithm relating said phase angle, V1 and V2 to said value.

18. A method as recited in claim 17, wherein said value comprises the capacitance of said reactive impedance.

19. A method as recited in claim 17, wherein said voltages applied to parts of said series circuit comprise the voltage applied across said series circuit and a voltage applied across said electrodes.

20. A method as recited in claim 17, wherein said arithmetic algorithm expresses said value as a function of said phase angle, said voltages, and said resistance.

21. A wood drying installation comprising
a wood drying kiln,
electrodes adapted to be inserted into wood contained in said kiln,
a resistance connected in a series circuit with said electrodes,
an AC voltage source connected to apply an AC voltage across said series circuit,
a phase detecting circuit connected to said series circuit operable to generate a signal representing a phase angle between AC voltages applied to different parts of said series circuit, and
a processor connected to receive said signal and operable to determine a value corresponding to at least one of an independent capacitive component and an independent resistive component of a reactive impedance between said electrodes in accordance with a predetermined arithmetic algorithm which expresses said value as a function of said phase angle, said voltages and said resistance.

22. A wood drying installation as recited in claim 21, wherein said voltages applied to different parts of said series circuit comprise a voltage applied across said electrodes and a voltage applied across said series circuit.

23. A wood drying installation as recited in claim 21, wherein said phase detecting circuit converts said AC voltages applied to different parts of said series circuit to square wave voltages and an exclusive OR circuit receiving said square wave voltages.

24. A wood drying installation as recited in claim 23, wherein said circuit further comprises an RMS-to-DC converter connected to receive an output of said exclusive OR circuit.

25. A wood drying installation as recited in claim 21, wherein said AC voltage source provides a sinusoidal voltage.

26. A method of measuring the moisture content of a stack of wood in a kiln comprising
placing electrodes in said stack of wood in said kiln, connecting a known series resistance in series with said electrodes,
applying a AC voltage across said series circuit,
detecting AC voltages applied to different parts of said series circuit,
determining a phase angle between said AC voltages applied to different parts of said circuit, and
calculating a value corresponding to at least one of an independent capacitive component and an independent resistive component of a reactive impedance between said electrodes in accordance with a predetermined arithmetic algorithm which expresses said value as a function of said phase angle, said voltages and said resistance.

27. A method as recited in claim 26, wherein said voltages applied to parts of said series circuit comprise the voltage applied across said series circuit and a voltage applied across said electrodes.

28. A method as recited in claim 26, wherein said independent capacitive component is calculated according to the equation $$C_x = -V_1 \sin \phi/(2\pi f R_s V_2)$$

wherein:
$C_x$ is the value of the independent capacitive component
$V_1$ is the amplitude of the applied voltage
$V_2$ is the amplitude of the voltage across the electrodes
f is the frequency of the applied voltage
$\Phi$ is the phase angle between the voltages $V_1$ and $V_2$
$R_s$ is the resistance connected in series.

29. A method as recited in claim 26, wherein said independent resistive component is calculated according to the equation $$R_x = R_s V_2/(V_1 \cos \phi - V_2)$$

wherein:
- $R_x$ is the value of the independent resistive component
- $V_1$ is the amplitude of the applied voltage
- $V_2$ is the amplitude of the voltage across the electrodes
- $\phi$ is the phase angle between the voltages $V_1$ and $V_2$
- $R_s$ is the resistance connected in series.

30. A method as recited in claim 26, wherein the moisture content of the wood is above a fiber saturation point of the wood.

31. A system for measuring the reactive impedance between electrodes which are inserted in a dielectric material, wherein said system comprises
- a resistance connected in a series circuit with said electrodes,
- an AC voltage source connected to apply an AC voltage across said series circuit,
- a phase detecting circuit connected to said series circuit operable to generate a signal representing a phase angle between AC voltages applied to different parts of said series circuit, and
- a processor connected to receive said signal and operable to determine a value corresponding to at least one of an independent capacitive component and an independent resistive component of said reactive impedance in accordance with a predetermined arithmetic algorithm which expresses said value as a function of said phase angle, said voltages and said resistance.

32. A system as recited in claim 31, wherein the voltages applied to different parts of said series circuit comprise a voltage applied across said electrodes and the voltage applied across said series circuit.

33. A system as recited in claim 31, wherein said phase detecting circuit converts said AC voltages applied to different parts of said series circuit to square wave voltages and an exclusive OR circuit receiving said square wave voltages.

34. A system as recited in claim 33, wherein said circuit further comprises an RMS-to-DC converter connected to receive the output of said exclusive OR circuit.

35. A system as recited in claim 31, wherein said AC voltage source provides a sinusoidal voltage.

36. A method of measuring the reactive impedance of a material comprising placing electrodes in said material, connecting a known resistance in series with said electrodes, applying a AC voltage across said series circuit, detecting AC voltages applied to different parts of said series circuit, determining a phase angle between said AC voltages applied to different parts of said circuit, and calculating a value corresponding to at least one of an independent capacitive component and an independent resistive component of the reactive impedance between said electrodes in accordance with a predetermined arithmetic algorithm which expresses said value as a function of said phase angle, said voltages and said resistance.

37. A method as recited in claim 36, wherein said voltages applied to parts of said series circuit comprise the voltage applied across said series circuit and a voltage applied across said electrodes.

38. A method as recited in claim 37, wherein at least one of said voltages comprises a sinusoidal voltage.

39. A method as recited in claim 36, wherein said independent capacitive component is calculated according to the equation $$C_x = -V_1 \sin \phi / (2\pi f R_s V_2)$$

wherein:
- $C_x$ is the value of the independent capacitive component
- $V_1$ is the amplitude of the applied voltage
- $V_2$ is the amplitude of the voltage across the electrodes
- f is the frequency of the applied voltage
- $\phi$ is the phase angle between the voltages $V_1$ and $V_2$
- $R_s$ is the resistance connected in series.

40. A method as recited in claim 36, wherein said independent resistive component is calculated according to the equation $$R_x = R_s V_2/(V_1 \cos \phi - V_2)$$

wherein:
- $R_x$ is the value of the independent resistive component
- $V_1$ is the amplitude of the applied voltage
- $V_2$ is the amplitude of the voltage across the electrodes
- $\phi$ is the phase angle between the voltages $V_1$ and $V_2$
- $R_s$ is the resistance connected in series.

* * * * *